United States Patent [19]
Andrews

[11] Patent Number: 5,346,826
[45] Date of Patent: Sep. 13, 1994

[54] PROCESS FOR CONDUCTING BIOCHEMICAL REACTIONS

[76] Inventor: Franklin T. Andrews, 824 Kainui Pl., Hailua, Hi. 96734

[21] Appl. No.: 423,800

[22] Filed: Oct. 18, 1989

[51] Int. Cl.[5] .......................... C12N 5/00; C12N 5/02; C12M 1/12
[52] U.S. Cl. .................. 435/240.241; 435/240.25; 435/240.4; 435/240.46; 435/243; 435/285; 435/286; 435/287; 435/311; 435/313; 435/315; 435/316
[58] Field of Search ............. 435/284–287, 435/311, 240.241, 240.242, 290, 313, 315, 240.25, 240.4, 240.46, 243, 316; 210/321.72

[56] References Cited

U.S. PATENT DOCUMENTS

| | | | |
|---|---|---|---|
| 3,186,917 | 6/1965 | Gerhardt et al. | 435/311 |
| 3,418,208 | 12/1968 | Coty | 435/311 |
| 3,472,765 | 10/1969 | Budd et al. | 210/321.72 |
| 3,856,475 | 12/1974 | Marx | 435/284 |
| 3,915,802 | 10/1975 | Kominek | 435/311 |
| 3,959,317 | 5/1976 | Gudin | 435/284 |
| 3,969,190 | 7/1976 | Hise et al. | 435/313 |
| 4,033,825 | 7/1977 | Haddad et al. | 435/284 |
| 4,220,725 | 9/1980 | Knazek et al. | 435/285 |
| 4,722,902 | 2/1988 | Harm et al. | 435/311 |
| 4,861,725 | 8/1989 | Liau | 435/288 |

Primary Examiner—James C. Housel
Assistant Examiner—Jan M. Ludlow
Attorney, Agent, or Firm—John J. Connors

[57] ABSTRACT

A process for growing procaryotic or eukaryotic cellular material in a tubular membrane immersed in an aqueous medium. The tubular membrane is filled with at least $10^2$ cells per milliliter at start-up and then maintained under controlled conditions to promote rapid growth of the cells so that the doubling time is less than 12 hours. A primary nutrient solution is continuously fed to the growing cells while some of the cells are being continuously withdrawn from the tubular membrane. The rate of cell removal is controlled so that that number of cells in the tubular membrane remains essentially constant at from $10^2$ to $10^{10}$ cells per milliliter and the production of metabolite byproduct remains the same under equilibrium conditions. Both cell material and metabolite byproducts are recycled.

6 Claims, 4 Drawing Sheets

PROCESS FOR CONDUCTING BIOCHEMICAL REACTIONS

BACKGROUND OF THE INVENTION

1. Field of the Invention

This invention relates to a process and bioreactor apparatus for conducting biochemical reactions under conditions that may be varied to optimize the production of selected products. Because conditions are readily controlled, and are easily varied, known products and products hitherto unknown are produced in the bioreactor apparatus of this invention.

2. Background Discussion

In U.S. patent application Ser. No. 06/939,818, filed Dec. 9, 1986, now abandoned entitled "Chemobiotic Tissue Culturing,? there is described a process (herein Folsome et al invention) for growing plants cells in a bioreactor. The plants cells are Grown under conditions that are independent of weather conditions, and therefore are not subject to the ravages of droughts, floods, frost, or wind. Soil and ground water pollution is eliminated because fertilizers and pesticides are not necessary. Depending upon the plant tissue cultures used as starting material, products produced by the Folsome et al invention may be made to exhibit the original color, taste, odor, and nutritional values of the plant from which the tissue culture is obtained. Products produced by the the Folsome et al invention can be manufactured the year round, maximizing existing packaging facilities. Production facilities employing the process of Folsome et al invention may be located anywhere in the world where water and energy are available.

SUMMARY OF THE INVENTION

The present invention is an improvement in the Folsome et al invention and provides the same advantages as the Folsome et al invention plus additional advantages.

The process of this invention provides a way of manufacturing foods, pharmaceuticals, and specialty chemicals from such bioreacting, living procaryotic or eukaryotic cellular materials such as yeast, molds, bacteria, and plant cells. For example, plant cells derived from tissue cultures are continuously produced, with two separate streams being created: a cell mass product stream and a metabolite byproduct stream, both of which may be recycled to improve yields. Virtually any living cellular material which grows in an aqueous medium provides the starting cells used in the process of this invention. In accordance with this invention, the cells are highly dispersed throughout the aqueous medium in either a uniform distribution of individual cells or as cellular aggregates. These cells reproduce continually and rapidly, and a portion of the cells are continuously removed from the cell mass product stream in order to maintain the cells in a logarithmic growth state. That is, so that the process yields twice the original number of cells present at start up within 12 hours. Because of this rapid growth, very expensive plant derived products may now be made by the process of this invention at a cost substantially lower than conventional practice. The cell mass produced by the process of this invention may have the same general characteristics as the plant from which the cells are derived or cellular material that has substantially different characteristics may be produced. Selection of conditions determines whether the process maximizes the yield of cell mass or metabolite byproduct.

With this invention, process conditions are varied until optimized to produce the maximum yield of the selected product, either cell mass or metabolite byproduct. A bioreactor of unique design enables the concentration of reacting ingredients to be easily altered on stream while the bioreactions are occurring. It includes monitoring equipment that detects the concentration of the reacting materials and products that need be controlled. The main parameter of the process which is varied is the concentration of nutrients. By increasing or decreasing nutrient concentration and various hormones and Growth promoters optimum Growth conditions are attained to produce the highest yield of the selected product with the most economical use of nutrients, a major cost of any biochemical process. The nutrients comprise a source of carbon (C), hydrogen (H), usually a sugar, oxygen (0), nitrogen (N), potassium (K), and phosphorous (P). There is more effective use of nutrients in the process of this invention because of recycling of both the cell mass product stream and the metabolite byproduct stream.

The cells are Grown in a reaction zone, preferably in the form of a tubular dialysis membrane, with the metabolic byproducts passing through the wall of the membrane into an aqueous medium in which the membrane is immersed. The nutrients are supplied to the cells by feeding an aqueous nutrient solution, referred to as the primary nutrient solution, to the cells inside the tubular membrane. The membrane has a pore structure that only allows chemicals with a predetermined molecular weight to pass through the membrane wall. This is referred to as the molecular weight exclusion range. The molecular weight exclusion range is selected based on the desired product to be produced. If a certain metabolite byproduct is to be produced having a relatively low molecular weight, a membrane is selected having an exclusion range that only allows such low molecular weight product to pass through the membrane wall. If the production of cell mass is the objective, the exclusion range is selected that allows very high molecular weight material to pass through the membrane wall, yet prevents the large diameter cellular material from passing through the wall.

The versatility of this invention is best illustrated by considering two cases. The first case is where the objective is to produce large quantities of cell mass. The second case is to produce a specific metabolite byproduct.

In the first case, the concentration of nutrients and the correct mix of nutrients in the primary nutrient solution is determined by changing the concentration and mix of nutrients until the highest yield of cell mass is achieved. The composition of the aqueous medium in which the tubular membrane is immersed is also established to favor cell mass production. When these conditions are determined, they are monitored along with the rate of cell mass production. If cell mass production decreases, the conditions are again changed to maximize yield. As metabolite byproducts are produced they pass through the wall of the membrane and are continuously removed from the bioreactor. The cell mass product is continually removed from the bioreactor at a controlled rate to maintain the cells in their logarithmic growth state. Thus, the selection of the products being removed and the rate of removal are controlled to create conditions which favor cell mass production and most economical use of nutrients.

In the second case, the concentration of nutrients and the correct mix of nutrients in the primary nutrient solution is determined by changing the concentration and mix of nutrients until the highest yield of metabolite byproduct is achieved. Also, the concentration of ingredients in the aqueous medium in which the tubular membrane is immersed are controlled to favor the production of metabolite byproducts. Again conditions are monitored and changed as needed to maintain the highest yield of metabolite byproducts with the most economical utilization of the nutrients.

The cells upon reaching a mature condition divide to produce two or more in, nature cells, which may be cell aggregates or individual cells. If conditions prevail were the concentration of aged, mature cells are the dominate population, clumping tends to occur, which may or may not represses the cell division. In order to keep the cells in the state favoring cell growth or metabolite production, individual cells or small aggregates (as opposed to clumps, which are relatively large masses of cells that block pumps or otherwise interfere with the operation of the process) are dispersed throughout the aqueous medium and the cell or small aggregate concentration is controlled so that the cells remain in their logarithmic growth state. This is, so that the concentration and age or other characteristics of cells does not tend to suppress logarithmic growth. As used herein, cells refer to both individual cells or small diameter aggregates of a number of cells.

This invention includes a process, bioreactor apparatus, and unique products produced in the bioreactor apparatus in which the process is conducted. There are a number of features of this invention, no single one one of which is solely responsible for all its advantages. Without limiting the scope of this invention, as it is expressed in the claims, its more prominent features will now be briefly discussed. After considering this discussion, and particularly after reading the section of this application entitled "DETAILED DISCUSSION OF THE PREFERRED EMBODIMENTS," one will understand how the features of this invention provide its advantages, which include, but are not limited to:
1. Ability to vary conditions of the process to control yield and quality of products.
2. Low cost of otherwise expensive plant derived products.
3. Ability to make plant derived products without need for conventional farming practices.
4. Optimal conversion and use of nutrients.
5. Uses a wide range of nutrient sources.
6. Ability to make products with a minimum amount of soil, ground water, and air pollution.

FEATURES

The first feature of this invention is that the cells produced by the process of this invention, while essentially the same as the source from which they are derived such as plants, frequently contain a greater proportion of the original plant's main characterizing ingredient. For example, red kidney beans, which normally contain around 42 percent protein, when groton by this process may contain as much as 80 percent protein. Because of this feature, many novel plant derived products may be produced by this process which have hitherto been unknown.

The second feature of this invention is that the cells are grown in a bioreactor which uses a flexible, semipermeable, tubular membrane. The primary nutrient solution is continuously fed to the cells growing in the tubular membrane. Conditions are controlled to promote rapid cell growth, with the cells in the logarithmic growth state so that the number of cells in the tubular membrane doubles within 8 to 12 hours. Extracellular metabolic byproducts are dialyzed through the membrane wall into the aqueous medium surrounding the tubular membrane. The cells can be conditioned to maximize the concentration of extracellular byproducts. The aqueous medium may be either water or a dilute nutrient solution utilizing some of the same ingredients as the primary nutrient solution, but containing from 10 to 50 times more water than the concentrated nutrient solution. When the live cellular material is derived from plants, the membrane is illuminated with light of sufficient intensity to allow photosynthesis.

The third feature is that the tubular membrane is made of standard membrane material such as, for example, cellulose acetate, polyacrlonitrile, or polysulfone. This eliminates the need for the development of special membrane materials. The physical dimensions of the tubular membrane are, however, important to attain the desired yields. Typically, the tubular membrane has diameters of from 0.25 to 3.0 inches, and lengths of from 1 to 8 feet. The exclusion range of the dialysis membrane depends upon the kind of cell mass product Grown, the extent of biofouling, and whether the desired product is the cell mass or the metabolite byproducts. Normally, an exclusion range of 500 to 1,000,000 Daltons is sufficient to retain most plant cells inside the tubular membrane while allowing most metabolite byproducts to diffuse into the aqueous medium. However, if a metabolite byproduct of a specific molecular weight is the desired product, the exclusion range of the tubular membrane is selected to accommodate the molecular weight of the desired metabolite byproduct. Although the preferred configuration of the membrane is tubular, other reactor designs are possible. Also, the tubular design allows for a bioreactor to comprise a tube within a tube to create inner and outer reaction zones. The cells may be grown in either the inner or outer reaction zone, although the inner zone is preferred. Different types of cells may be Grown simultaneously in each zone. The concentration of nutrients is maintained at the correct levels for each specific type of cell mass product through introduction of nutrients dissolved in water into either the inner or outer reaction zones. The selection of the exclusion range and concentration of ingredients in the primary solution and aqueous medium is determined so that that the optimum growth rate for the selected product is achieved.

The forth feature is that the process grows cells continuously. Cells are constantly withdrawn from the tubular membrane at the same rate that new cells are grown. To do this the cell population inside the tubular membrane must be kept at an essentially constant level. Most cells have a critical population level below Which they will not grow in the tubular membrane. It has been discovered that for most cellular material the minimum concentration of cells at start-up is at least $10^2$ cells per milliliter, and preferably ranges from $10^2$ to $10^7$ cells per milliliter. The cells may be either very large or very small, and therefore, cell count is not necessarily the only way to characterize conditions of the process. An alternate way is by the mass fraction of cellular material compared to the total weight of material in the membrane. Using this approach the start up concentration of cells is from 0.0005 to 0.01 mass fraction.

The fifth feature is selective cell removal, which is accomplished by installing a cell separating device on the effluent cell mass product stream from the tubular membrane which separates the cells by size. Cell removal is controlled so that the cells are withdrawn from the tubular membrane at a rate sufficient to prevent metabolite and competitive repression of the growth of the cells. In general, this entails removal of either aged mature cells or clumps.

The sixth feature is to recycle cells exiting from the tubular membrane back to the influent end of the tubular membrane so that they may grow larger, divide and multiply, thereby increasing the yield.

The seventh feature is to recycle the metabolite byproduct stream to increase the concentration of metabolites in the metabolite byproduct stream. The metabolite byproducts are separated from the metabolite byproduct stream and this stream is recycled.

The eighth feature is to tailor the ingredients and concentration of ingredients in the primary nutrient solution to provide the greatest possible yield of cell mass or metabolite byproduct, depending on the desired product. The portion of the plant which yields the desired product is freshly harvested, and a small section of this plant is excised and cultured in accordance with conventional practice to produce the cells used at startup of the process. These cells are grown using several different nutrient solutions to determine which nutrient solution composition produces the fastest cell growth. Of the several different solutions screened, the nutrient solution composition producing the fastest cell growth is used as the primary nutrient solution which is fed to the cells in the tubular membrane. Although this screening may be done prior to introducing the cells into the bioreactor, one of the advantages of the bioreactor is that the screening preferably is accomplished on stream in the bioreactor by simply monitoring the yield of the desired product as the concentration and mix of nutrients is altered in either the primary nutrient solution or aqueous medium, or both.

The ninth feature is to chemically tailor the dilute nutrient solution to increase the yield of the desired product in the metabolite stream. Typically, the primary nutrient solution is simply diluted with water, usually using from 10 to 50 times more water than is present in the primary nutrient solution. In some instances, the dilute nutrient solution may contain no carbon and hydrogen source (sugar), and only contain a source of nitrogen, potassium and phosphorous.

The tenth feature of this invention is that the dilute nutrient solution provides a nutrient back-up source for the cells growing inside the tubular membrane. As the cells grow in the tubular membrane nutrients are consumed. Consequently, there may be insufficient nutrients available to downstream cells. The nutrients in the dilute nutrient solution move across the wall of the membrane into the interior of the membrane to supply the downstream cells.

The eleventh feature is to maintain a higher pressure either inside or outside the dialysis tubes to obtain the most favorable osmotic pressure gradient to increase the yield of the desired product. For example, if excess metabolite byproduct is in the cell mass product stream, the pressure inside the membrane is increased to force the metabolite byproduct across the membrane wall and into the aqueous medium. If excess nutrient is in the aqueous medium, the pressure on the aqueous stream is increased to force the nutrients into the membrane. The pressure across the membrane is varied by changing the applied physical pressure on either side of the membrane or by altering the osmotic pressure by changing the concentration of ingredients in either the primary or dilute nutrient solutions. The pressure in controlled to achieved the highest yield of the desired product.

The twelveth feature of this invention is to control the physical and chemical conditions of the process to provide optimum yields of product. Each particular product being made by the process of this invention will require different conditions to optimize the yield. Some of the more important variables to be controlled are:

a) The ingredients and concentration of ingredients in the primary nutrient solution.
b) The ingredients and concentration of ingredients in the dilute nutrient solution.
c) The pH of the primary nutrient solution and aqueous medium. The pH of the concentrated nutrient solution under aerobic conditions is maintained in a range from 3.0 to 8.0, and under anaerobic conditions is maintained in a range of from 6.0 to 11.0. The pH of the dilute nutrient solution may be the same or different as the primary nutrient solution.
e) The temperature. The temperature of the nutrient solutions is maintained in a range from 50 to 75 degrees Fahrenheit.
f) Velocity of the concentrated nutrient solution. Concentrated nutrient solution velocity through the tubular membrane is within the range of 0.005 to 3.0 feet per minute.
g) The velocity of the aqueous medium. The aqueous medium velocity across the exterior surface of the tubular membrane is in the range of 0.005 to 5.0 feet per minute.
h) Cell concentration in the effluent. The effluent from the tubular membrane has a cell concentration within the range of $10^2$ to $10^{10}$ cells per milliliter or a mass fraction of from 0.005 to 0.15.
i) The aerobic or anaerobic environment. Gas containing oxygen is percolated through the tubular membrane if the cell metabolism is aerobic. Gas containing nitrogen, carbon dioxide, or a mixture of nitrogen and carbon dioxide is percolated through the tubular membrane if the cell metabolism is anaerobic. Gas under pressure is forced through the tubular membrane. The pressure may be varied to flex the membrane, thereby agitating the membrane wall to remove cell material that may prevent dialysis across the membrane wall.

The thirteenth feature of this invention is that different cell types may be simultaneously introduced into the tubular membrane to produce a unique cell product having distinctive taste, color, odor and nutritional characteristics.

The preferred embodiments of this invention illustrating all its features will now be discussed in detail. These embodiments employ Garlic as the plant from which both cell mass product and metabolite byproduct are derived, but other living cells and metabolite byproducts have been produced by the process of this invention, including:

red kidney bean
carrots
clover
lima beans wheat
corn
yeast, for example, saccharomyces cerevisiae

BRIEF DESCRIPTION OF THE DRAWING

The process of this invention, the bioreactor used to carry out the process of this invention, and the garlic cell mass product produced by the process of this invention are shown in the accompanying drawing, which is for illustrative purposes only, and in which.

DETAILED DESCRIPTION OF PREFERRED EMBODIMENT

First, select a portion of a plant which contains the desired product, either cell mass product or metabolite byproduct, and then culture this selected portion in accordance with conventional culturing techniques to provide plant cells used at start-up. A section from a garlic bulb, cultured in accordance with the following culturing protocol, provides garlic cells which are grown by the process of this invention in the apparatus depicted in the FIGS. 1 and 2.

GARLIC PROTOCOL

Garlic (allium sativum L.) is an excellent example of the type of cell product that may be made by the process of this invention, because it is easy to culture, the cell mass produced retains garlic's characteristic color, odor and taste, and the strengths of these characteristics are enhanced by the process of this invention.

Figure 1:
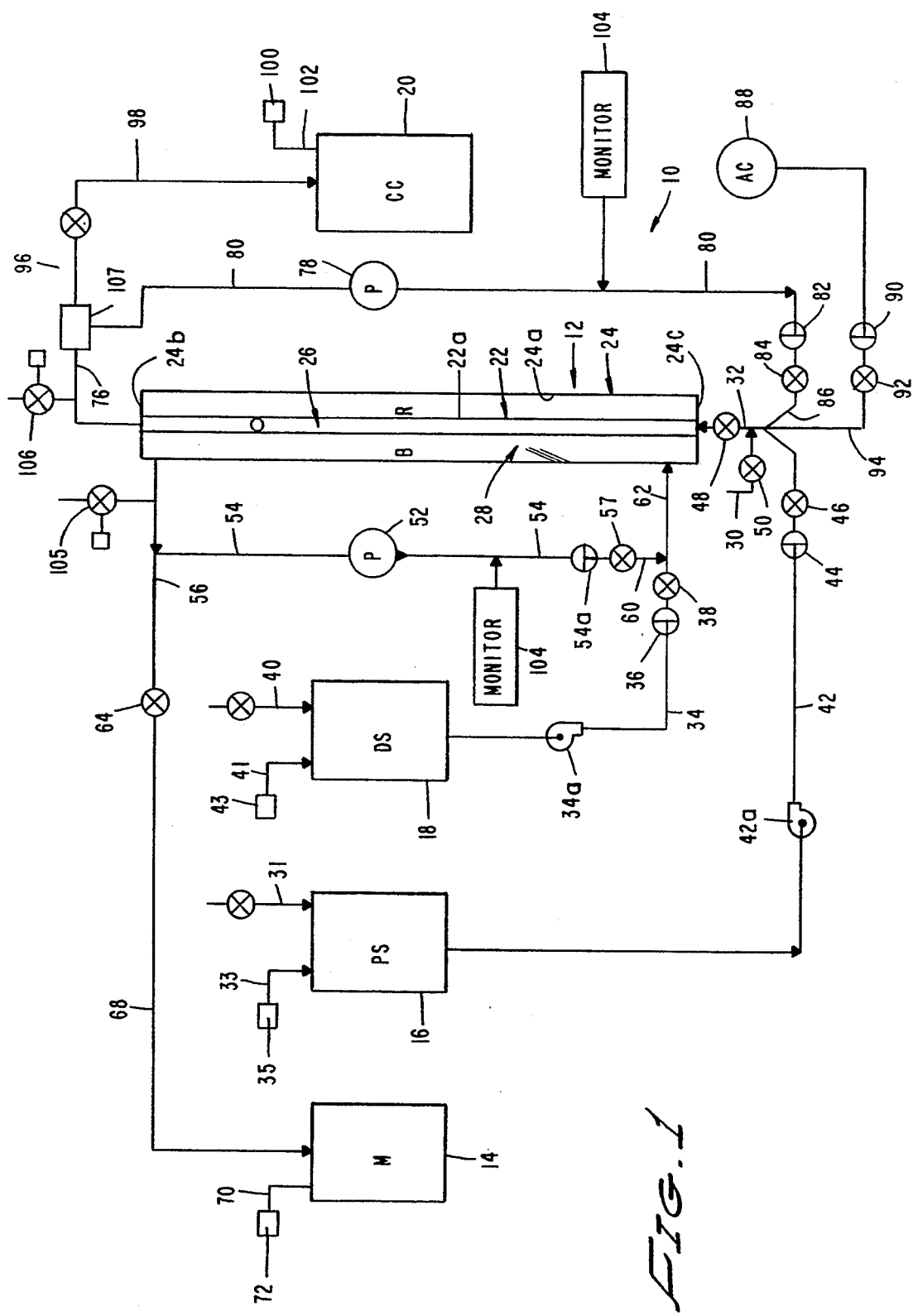
FIG. 1 is a schematic diagram showing a small scale demonstration unit for carrying out the process of this invention.
Figure 3:
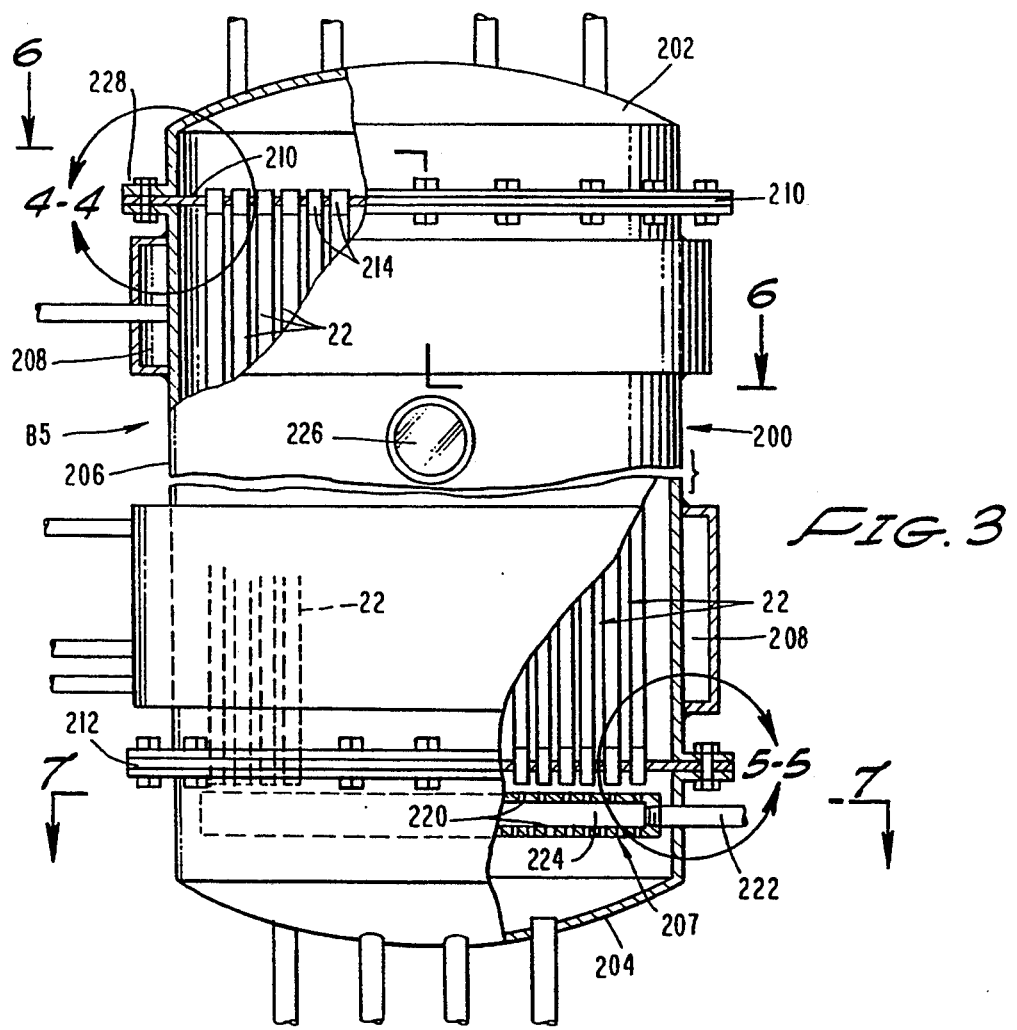
FIG. 3 is a side elevational view, with sections broken away, of the bioreactor used in the production facility shown in FIG. 2.

Preparation of Cell Culture a) The first step is to break open a fresh bulb of garlic and select a clove as the source of an explant.

b) Under a sterile hood with a sterile scalpel and tweezers remove the clove's paper thin covering and soak it in a 90% ethanol solution for 5 minutes and a 5 to 10% Chlorox solution for 5 to 10 minutes. Next, wash the clove thoroughly with sterile distilled water and place it in a sterile petri dish.

c) Hold the clove in the tweezers over a petri dish and with the scalpel, cut deep into the center of the clove and remove the apical meristem tissue.

d) Take a number bits of about 0.2 to 0.5 mm each from the sterile garlic tissue and place into a modified Murashige-Skoog nutrient medium containing 2 ppm of 2,4, dichlorophenoxyacetic acid and solidified with 0.6 to 0.8% of Difco Bacto Agar on the bottom of 250 ml Erlenmeyer flask. The use of the 2, 4, dichlorophenoxyacetic acid need not be used once the cells are growing in the bioreactor shown in FIGS. 1 and 2.

e) Incubate the sections in the dark or low light at 25–28 degrees Centigrade. After 3 or 4 weeks the callus should be about twice the size of the original explant. Solid medium cultures are used to preserve desirable cell lines.

f) To prepare suspension cultures, the kind used in the bioreactor depicted in FIGS. 1 and 3, the sterile garlic bits obtained in steps (b) and (c) are placed in 250 ml Erlenmeyer flasks containing a modified, liquid Murashige-Skoog medium of the same composition as step (d) but without agar.

g) Place multiple flasks on a shaker for 4 to 6 weeks and watch for cell growth. The rate of growth, color, odor, taste and nutritional value of the cells is compared to original tissue, which is the measure of the efficiency of the culturing media. Such characteristics are measured by sampling cells from the different flasks.

Preparation of Nutrient solutions

The primary nutrient solution is prepared using conventional screening methods. This may be done as illustrated in the following example to determine what primary nutrient solution to use at start-up, and then the composition of the primary nutrient is varied while the process is being conducted in the bioreactor to optimize for highest yield of the desired product, either cell mass or metabolic by product.

In the literature there is set forth the protocol for culturing most well known plants. Each protocol identifies the mix of ingredients and concentration of ingredients of the preferred nutrient solution for the culture explant selected. This is the starting nutrient solution which is modified as required to produce the highest yields of products with all the desirable characteristics of the original plant tissue made by the process of this invention.

The primary nutrient solution comprises water in which are dissolved inorganic nutrients, organic nutrients, and Growth promoters. By varying the composition and concentration of these ingredients and screening, the optimum primary nutrient solution is obtained.

The principal inorganic nutrient elements are nitrogen (N), phosphorus (P), potassium (K), calcium (Ca), sulphur (S), and magnesium (Mg), which are used in millimolar quantities, and boron (B), copper (Cu), iron (Fe), maganese (Mn,) molybdenum (Mo), and zinc (Zn), which are used in micromolar quantities. The concentration of these nutrients remain fairly constant for growing for most plant cell and usually are not changed in the initial screening. When the process is on stream, however, they are varied to optimize yields.

The principal organic nutrient element is carbon from sugars, starch, or algae. Coconut milk and casein hydrolsolate may also be used as an extra source of carbon. In some cases, carbon dioxide can be used.

The growth promoters are, for example, hormones, phytohormones and vitamins. The vitamins, hormones and phytohormones are most important for cell division and growth, and vary widely with each type of cell. Thiamine is important for most plants. Nicotinic acid, gibberelin (a phytohormone) and pyridoxine (a B-complex vitamin) are also used for growth improvement. The phytohormones, especially the cytokinins and auxins, are of greatest importance in inducing mitosis and regulating cell growth. The cytokinin most often used is kinetin which occurs naturally in most plants. Other cytokinins used are zeatin, benzyladenine, and isopentyl adenosine. Auxins most often used are 2,4dichlorophenoxyacetic acid, napthaleneacetic acid 2,indolephenoxyacetic acid, and indolebutyric acid.

The best nutrient solution for any kind of cells must be determined by using different hormone modifications and ratios of the standard Murashige-Skoog, Gamborg solutions, or with specially prepared media. For example, due to rapid cell growth in the bioreactor, greater than normal concentrations of carbon source can be used.

EXAMPLE

Small bits of garlic cells prepared according to the protocol are transferred to each hole of a 98 hole Falcon test tray containing the different nutrient solutions to be tested. Six replications of each solution were tested to indicate individual solution effectiveness. The test trays were monitored weekly over a six week period to evaluate the particular solution that grew the greatest amount of cells.

The next step was to prepare a sufficient amount of sterile garlic cells in the optimized, sterile nutrient solution. Garlic bits having a diameter of 0.5 millimeter or smaller, were placed in Erlenmeyer flasks containing 100 ml of the optimum nutrient solution. The flasks were placed on shaker table and within 5 weeks the garlic formed a suspension culture which was transferred to the demonstration unit shown in FIG. 1. The optimum sterile primary nutrient solution and aqueous medium are then developed "in site" in the bioreactor to produce the highest yield of the desired product.

The Start-Up Garlic Primary Nutrient Solution

The composition of the start-up garlic nutrient solution developed by the screening procedure described above and tested in the demonstration unit depicted in FIG. 1 is as follows:

| Nutrient Source | Nutrient Provided | Concentration (mg/liter) |
| --- | --- | --- |
| Ammonium Nitrate | Nitrogen | 1650 |
| Potassium Nitrate | Potassium/Nitrate | 1900 |
| Calcium Chloride | Calcium | 330 |
| Potassium Phosphate | Potassium/Phosphorus | 170 |
| Magnesium Sulphate | Magesium/Sulfur | 181 |
| Potassium Iodide | Iodine | 0.83 |
| Ferric Sulphate (EDTA) | Iron | 36.7 |
| Manganese Sulphate | Manganese/Sulfur | 16.9 |
| Boric Acid | Boron | 6.2 |
| Sodium Molybdenate | Molybendum | 0.25 |
| Cobalt Chloride | Cobalt | 0.025 |
| Copper Sulphate | Copper | 0.025 |
| Sucrose | Carbon | 30,000. |
| HORMONES AND VITAMINS | | |
| i-Inositol | | 100.0 |
| Indole-3-acetic acid (IAA) | | 1.0 |
| Thiamine | | 0.4 |
| Glycine | | 0.4 |
| Kinetin | | 5.0 |
| (2-Isopentenyl) adenine (2iP) | | 7.5 |
| Naphaleneacetic Acid (NAA) | | 1.0 |
| Pyridoxine.HCl | | 0.1 |
| Niacin | | 0.1 |
| 2,4 Dichlorophenoxyacetic Acid (2,4-D) | | 2.0 |
| Coconut Milk (% volume/volume) = 5.0 | | |

Start-Up Garlic Dilute Nutrient Solution

The dilute solution used in the demonstration unit shown in FIG. 1 to Grow Garlic cells contained 10 times more water than the concentrated solution described above.

Demonstration Unit

As shown in FIG. 1, the demonstration unit 10 includes a bioreactor 12, a metabolite holding tank 14, a primary nutrient solution holding tank 16, a dilute solution holding tank 18, and a cell collection tank 20. The bioreactor 12 comprises a dialysis tube or an inner tubular dialysis membrane 22 and an outer cylindrical vessel 24 which contains the aqueous medium, in this case the dilute nutrient solution in the tank 18. The arrangement of the tubular membrane 22 within the vessel 24 provides an inner reaction zone 26 within the membrane and an outer reaction zone 28 in the space between the wall 24a of the vessel and the wall 22a of the membrane. The ends 24b and 24c of the vessel are closed and sealed at the junction with the membrane wall 22a. The bioreactor 12 is vertically oriented, but may be tilted at an angle.

The tubular membrane 22 is initially filled with cultured plant tissue through the valve line 30 and valve line 32 to the lower end of the tubular membrane 22. It is important that a sufficient number of plant cells be present inside reaction zone 26. Enough cells must be present so that they will divide and multiply to maintain a minimum cell growth rate. Thus, the minimum concentration of cells inside the inner reaction zone is $10^2$ cells per milliliter. Depending upon the diameter of the cells, the initial charge may range between $10^2$ to $10^7$ cells per milliliter (mass fraction of from 0.0005 to 0.05). Dilute nutrient solution from the holding tank 18 is pumped by pump 34a through the line 34 to the check valve 36 and open valve 38 into the inside of the vessel 24 to fill the outer reaction zone 28 with dilute nutrient solution. Make up dilute solution is fed through the valve line 40 into the top of the tank 18. Tank 18 has an air escape line 41 equipped with a sterile filter 43.

Primary nutrient solution is fed from the holding tank 16 and pumped by pump 42a through line 42 through the check valve 44 and open valve 46 in line 42 and the open valve 48 in line 32 to the inside of the tubular membrane 22. Once the inner reaction zone 26 is filled with a sufficient quantity of plant cells, the valve 50 in line 30 is closed. The valves 46 and 48 in lines 42 and 32, respectively, are kept open as long as the process is running, continuously feeding the primary nutrient solution to the inner reaction zone 26 to replenish nutrients as they are used up by the metabolic reaction of the cells growing inside the inner reaction zone. Make up primary solution is added through valved line 31 and air escapes through line 33 which equipped with a sterile filter 35.

As the cells grow within the inner reaction zone 26 the byproducts of the metabolism, the metabolite byproducts, move across the membrane wall 22a into the dilute nutrient solution in the outer reaction zone 28. This dilute nutrient solution is continuously pumped by the pump 52 in line 54, moving it through the outer reaction zone 28 out the top of the reaction zone through line 56 and line 54 to the input end of the pump 52 then out the output end of the pump through the check valve 54a and open valve 57 in line 60 into line 62 to be recycled to the lower end of the vessel 24. Make up solution may be added to this recycling stream of dilute nutrient solution by opening the valve 8. The check valve 36 prevents the recycling dilute nutrient solution from backing up into or flowing into the holding tank 18. When it is desired to draw off metabolite byproduct, the valve 64 in line 68 is opened and a portion of the recycle stream is directed by line 68 into the metabolite holding tank 14. A gas escape line 70 with a sterile filter 72 at its end allows air to escape from the metabolite holding tank as it is filled with metabolite product from the outer reaction zone. Two pressure relief valves 105 and 106, one in line 56 and the other in line 76, allow Gaseous products to escape.

The cell product stream from the inner reaction zone 26 flows out the top of this zone through the line 76 as it is pumped by the pump 78 through line 80, check valve 82 and open valve 84 in line 86 into the bottom of the inner reaction zone 26. Thus the cell product stream is separated by cell separator 107 into small cells and clumps. After the clumps, the remaining cells are continuously recycled by the pump 78. Compressed air from an air compressor 88 is forced through a check valve 90 and open valve 92 in line 94 and open valve 48 in line 32 into the bottom of the inner reaction zone 26 to percolate small bubbles of air including oxygen through the inner reaction zone. This maintains an aerobic environment within the inner reaction zone 26. If desired, the conditions could be changed to maintain an anaerobic environment. Gas, however, would always be forced under pressure through the inner reaction zone 26 to create an ebullient gaseous environment to enhance the Growth rate of the cell mass product within the inner reaction zone.

The following table sets forth the typical conditions maintained within the bioreactor 12 using a 36 inch long dialysis tube with a 0.5 inch diameter for a garlic cell product of the type manufactured in the demonstration unit 10 when the garlic cells of the Example are placed in the inner reaction zone 26 of the bioreactor.

TABLE

| | |
|---|---|
| Temperature | 25° C.–27° C. |
| pH | 5.0–5.3 |
| Velocity Inside Tube (recycle) | 0.005–0.05 feet/minute |
| Velocity Outside Tube (recycle) | 0.005–0.1 feet/minute |
| Cell Count | $1.5 \times 10^7$ cells/milliliter |

When it is desired to collect cell mass product the valve 96 in line 98 is opened and a portion of the cell mass product stream is directed through the line 98 into the cell collection tank 20. This tank 20 has a sterile filter 100 in line 102 which allows air inside the tank to escape as the tank is filled with collected cell mass.

In accordance with this invention, the cell mass product stream flowing through line 80 and the metabolite byproduct stream flowing through line 54 are monitored to determine the chemical composition of these streams. Preferably, Fourier Transform-Infra Red (FT-IR) spectrometers 104 of the type sold by Applied Power Concepts, Inc. of Irvine, Calif. are used. Upon changing the concentrations of nutrients in the primary and dilute solutions, yields of cell mass product and metabolite byproducts are altered until the correct mix and concentrations of nutrients are developed to produce the highest yield of desired product. Thus, the demonstration unit 10 provides a quick and inexpensive means of:

a) checking the efficiency of the nutrient solutions.

b) growing small quantities of cell mass for test purposes.

c) obtaining preliminary engineering data for the design of a pilot plant.

d) changing process parameters quickly to improve cell growing techniques.

e) providing the initial pilot plant bioreactor cell charge.

Operation of Demonstration Unit

First, all lines, tanks, vessels, and equipment are sterilized and then the primary and dilute nutrient solution tanks 16 and 18 are filled. All valves are closed and the main air line 94 is charged at 3 to 4 psi of air pressure.

Next, about 180 ml of fresh garlic cells produced in accordance with the EXAMPLE at a concentration of $1 \times 10^5$ cells per milliliter is introduced into the bioreactor 12 through the valves 50 and 48 in line 32. Air from compressor 88 is injected into the bottom of the tubular membrane 22 by cracking the valve 92 on line 94. Pumps 34a and 42a are started. Then, valves 46 and 48 on lines 42 and 32 are opened to allow solution to enter the bottom of membrane 22. Next, the valves 38 and 57 on lines 34 and are opened to allow dilute solution from the tank 18 to flow into the outer reaction zone 28.

At start-up the solution levels inside and outside the membrane 22 are kept the same until the cell count is $10^7$ cells per milliliter. At this point cells can be withdrawn to the cell collection tank 20. After the growing operation is underway, recycling of cell mass product and metabolite byproduct may be activated by opening the valves 57 and 84 and starting the pumps 52 and 78.

Cell mass and metabolite samples are taken periodically and analyzed for sugar content, pH, cell count and cell diameter, carbon dioxide, and dissolved oxygen. Preferably. the FT-IR spectrometer is used, with sampling and adjustment of process conditions being under computer control. Tests were performed in the demonstration unit 10 illustrated in FIG. 1. using the described nutrients solutions and a bioreactor 12 with ½" diameter dialysis tube, 36 inches long, produced 3.2 grams of Garlic with a 12% moisture content in 9.3 hours.

Large Scale Production Facility

Figure 2:
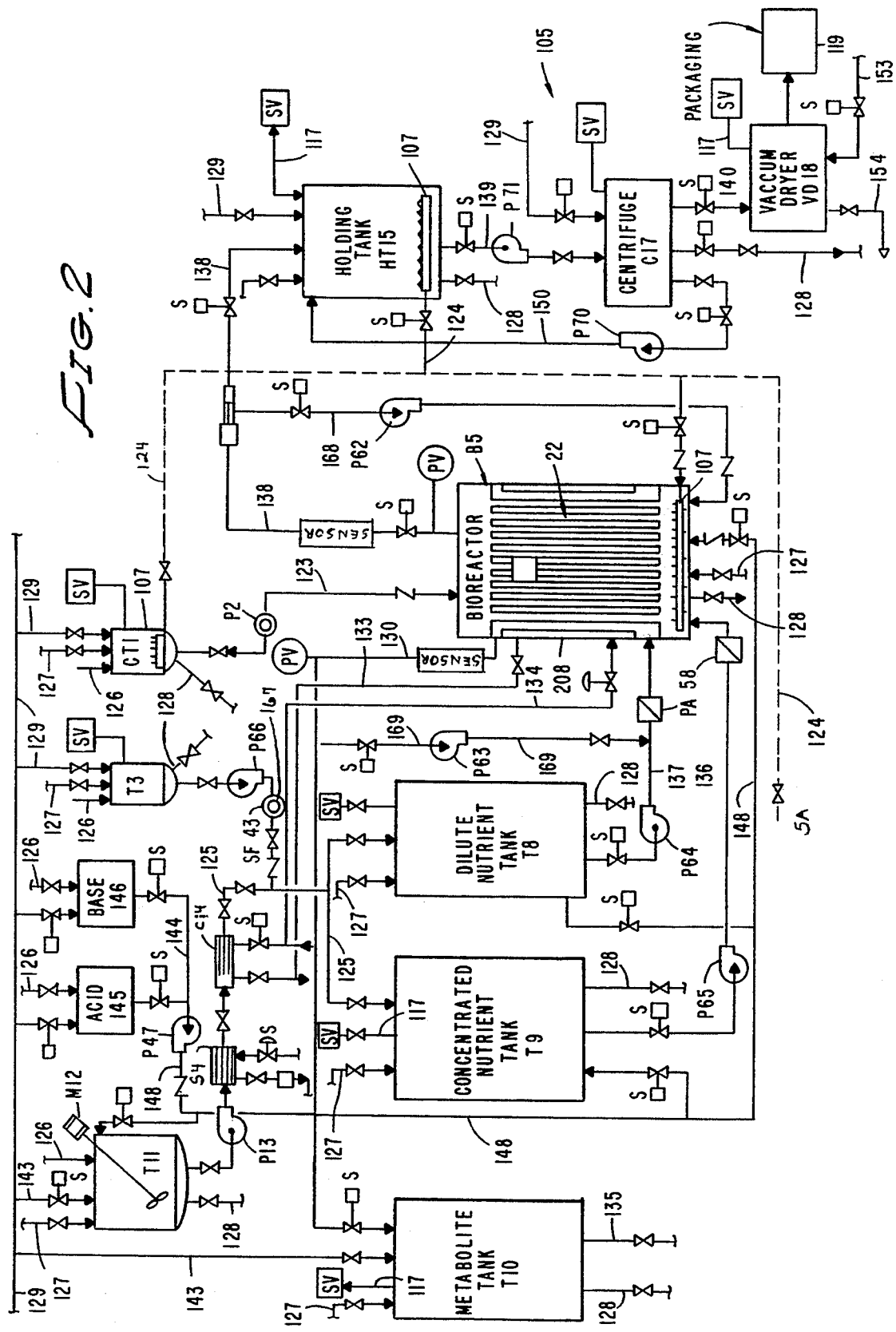
FIG. 2 is a schematic diagram showing a large scale production facility using the process of this invention.

The design for the production facility 105 illustrated in FIG. 2 is based upon the experience obtained from the design and operation of the demonstration unit 10. In this facility 105, the wetted surfaces of all equipment, the parts thereof, controls, and conduits are capable of withstanding steam sterilization and corrosion from the specific chemicals used in the process. In most instances, this means No. 316 stainless steel or polycarbonate polymeric material is used in their construction. The symbol "S" denotes a solenoid control valve.

All equipment and lines are sterilized before operations can begin.

Cell Culture Supply Tank CT1

The first step is to fill Tank CT1 with a suspension of garlic cells from the demonstration unit 10. Air is supplied through line 124 to sparger 107 for agitation and enhancement the metabolic process. The symbol "SV" denotes a sterile vent and "SA" denotes sterile air.

Cell culture density is checked by drawing off samples through drain connection 128. When analysis indicates that cell count is above the critical mass required for rapid cell growth, the garlic cell suspension is pumped by pump P2 through line 123 into bioreactor B5.

Line 127 is for sterilizing by steam, or chemical sterilents such as ethylene oxide or sodium hypochlorite. Line 129 is to adjust cell density of the culture tank with sterile deionized water or wash out the system after charging the bioreactor or sterilization.

Bioreactor B5

The bioreactor B5 is the heart of the process. It is inside the dialysis tubes 22 supplied with concentrated nutrient solution from Tank T9 that cell growth and division occurs. Excess air for metabolic purposes is introduced into the dialysis tubes 22 through line 124 and sparger 107. Some air is directed towards the bottom of the bioreactor B5 to prevent cell build-up. The air agitates the cells and increases the rate of replication by constantly bathing them with fresh nutrient solution. Air also reduces biofouling on the inside walls of dialysis tubes 22, assisting in the transference of metabolic products into the dilute nutrient (metabolite) stream. Both of these reactions reduce the time for cell replication.

Concentrated nutrient solution from Tank T9 is supplied by pump P65 into the bottom of the bioreactor B5 through line 136 in an amount needed to replenish the amount of solution and newly grown cells removed to holding tank HT15. Dilute nutrient solution is pumped by pump P64 to the bioreactor B5 from Tank T8 through line 137 in an amount determined by the analysis in a monitoring system to be necessary to produce either the desired cell mass or metabolic byproduct in greatest amount and in the least amount of time.

The pH in the bioreactor B5 in which grow the garlic cells is maintained at about 5.4 by adding either acid or base by pump P47 through lines 144 and 148. Sodium hydroxide and hydrochloric acid may be used, but they create sodium chloride, which may be harmful to some plant cells. Therefore, the preferred acid and base in most instances are nitric acid and potassium hydroxide, which produce the salt potassium nitrate, a nutrient. Garlic cells are removed to holding tank HT15 through line 138 in order to maintain the efficiency of the bioreactor.

Newly grown cells (clumps removed) are recycled at the optimum rate (+or− 50%) through line 168 by pump P62 to the bottom of the bioreactor B5. Metabolites are also recycled at the rate required for the maximum build-up of the desired product in the metabolite stream through line 169, pressure alternator PA58 and line 137 by pump P63.

Different kinds of cells demand different temperatures for optimum growth. Tests on garlic cells indicates that they do very well when grown between 60 and 65 degrees Fahrenheit. To maintain this temperature inside the bioreactor B5, cooling water is introduced into jackets 208 through line 134 and leaves through line 133.

Pressure alternators PA58 in lines 136 and 137 alternate the pressure to expand or flex the dialysis tubes 22 to slough off any cell materials which might cling to the walls of the tubes and prevent the transfer of nutrients or metabolic products. Line 127 is the bioreactor's sterilent wash connection. Line 128 is its sample test and drain connection.

In a production facility designed for the commercial production of garlic, batteries of parallel bioreactors B5 may be desired.

Cell Holding Tank HT15

The main purpose of this tank HT15 is to hold-up the effluent from the bioreactor B5 and grow the cells to a greater size and weight before the cells are centrifuged or separated. Line 138 carries the newly grown garlic cells from the bioreactor B5 to the holding tank HT15. The atmosphere in tank HT15 is 15 psig and sterile vented through line 117 of the excess sparger air and carbon dioxide created in the bioreactor B5 and the holding tank itself. Line 124 provides sparger air, line 126 is the sterilent connection and line 129 supplies sterile deionized water.

Centrifuge C17

Centrifuge C17 separates the cells from the nutrient solution. Its second purpose is to return the smaller cells still in the nutrient solution back to the holding tank HT15 by pump P70 and line 150. Its third purpose is to wash the centrifuged cells and remove all traces of the nutrient solution from them. The mixture of cells and nutrient solution is pumped from the holding tank HT15 through line 139 by pump P71 into a rotating basket screen (not shown) inside the centrifuge C17. Then, the relatively dry cell mass clinging to the side of the basket is sprayed with sterile deionized water from line 129 to remove the last vestiges of nutrient solution. Unless the economics are favorable, the wash water is wasted to the sewer through line 128.

Vacuum Dryer VD18

The equipment required for the last two operations depends upon the final form the product is to take. Assuming that it is to be a powder the cell mass from the centrifuge would be conveyed through line 140 to a vacuum dryer VD18 where the Garlic cells would be dried to a powder with a moisture content no Greater than about 10 percent. Steam for drying is supplied to a heating coil through line 153 and its condensate is returned to the boiler through line 154. Moisture and air would be sterile vented through line 117 and sterile vent SV. Line 154 is for draining the dryer. Packaging the Garlic will be done in operation 119 in the kind of container customarily used by a food processing manufacturer.

Metabolite Tank T10

Tank T10 collects the Garlic metabolites from the Bioreactor B5 through line 130 and stores them for further processing for valuable byproducts. Line 117 contains a sterile vent through which air is inhaled or exhaled during unloading or filling. Line 127 is the sterilent connection and 128 the sample-drain connection. Line 135 is the unloading connection and line 143 is the sterile deionized wash-water connection.

Concentrated Nutrient Solution Tank T9

Tank T9 receives the concentrated nutrient solution from mixing tank T11 through line 125 and stores it for delivery to the bioreactor B5 through line 136 by Pump P65. Line 117 is the necessary sterile vent, line 127 the sterilent connection, line 128 is the sample-drain connection and line 125 is the means by which sterile vitamins, hormones, and deionized water are delivered. Deionized water is used for concentration adjustment or wash down. Line 148 provides acid or base for the adjustment of the pH.

Dilute Nutrient Solution Tank T8

Tank T8 receives the dilute nutrient solution from mixing tank T11 and stores it for use in the bioreactor B5. Line connections are identical to those of tank T9 except for line 137 which delivers the dilute nutrient solution PA58 by means of pump P64 to the bioreactor B5. Pressure alternator on line 137 is the means by which the dialysis tubes 22 are flexed to slough off any cell material which might clings to the tube walls.

ANCILLARY EQUIPMENT

Nutrient Mixing Tank T11

The macro and micro salts required for the garlic's nutrient solutions are preweighed and mixed by mixer M12 with the correct amount of deionized water in tank T11. The pH of the mixture is adjusted by pumping either acid or base from Tanks 145 and 146 by pump P47 through lines 144 and 148. When ready, the mixture is pumped by Pump P13 through line 125 to sterilizer S4 then cooler C14 where it is reduced to ambient temperature before entering concentrated nutrient supply tank T9.

The dilute nutrient solution for the garlic is made in the same way as the concentrated solution except that amount of sterile deionized water used is ten times greater.

Line 126 is the conduit through which the preweighed nutrient salts are added to tank T11. Line 127 is the sterilent line and line 143 is for the addition of deionized water. Line 128 is the sample-drain connection.

Vitamin and Hormone Mixing Tank T3

The hormones and vitamins are mixed separately and added directly to the nutrient supply tanks T8 and T9 because they decompose under heat and must be filter sterilized. The vitamins and hormones are solvated and added to tank T3 through line 126. If necessary additional sterilized deionized water can be provided through line 129. When ready, the mixture of hormones and vitamins are supplied by pump P66 through line 167 and sterile filter SF43 into line 125 and then to the nutrient supply tanks T8 and T9. To insure thorough mixing in these tanks the vitamin and hormone mixture should be pumped into tanks T8 and T9 before the nutrient solutions from tank T11 are pumped into them. Line 127 is the sterilent connection and line 128 the sample-drain connection.

pH Adjustment Tanks T45 and T46

The nutrient solutions are adjusted to a pH range between 5.2 and 5.6 for optimum garlic cell growth. This is accomplished by supplying either acid or base directly from tanks 145 and 146 to mixing tank T11 in the proper amount through pump P47 and lines 144 and 148. The pH of the cell solution inside the dialysis tubes 22 of the bioreactor B5 has a tendency to rise during metabolism. To maintain a constant pH, acid is added to the bottom of the bioreactor B5 through line 148. Line 126 is the acid or base fill line for tank 145 or tank 146. Line 143 is for the addition of sterilized deionized water as either a dilutant or wash-water. Nutrient supply tanks T8 and T9 can be washed down through the pH adjustment tanks 145 and 146 or the mixing tank T11. Line 127 is the sterilent connection and line 128 the sample drain connection.

Process Control

Bioreactor B5 is the principal point of control for the entire process. Sensors in exiting cell mass line 138 monitor and control the flow rate, the number of cells per milliliter, the separation and recycling of the cells according to their size, pH, temperature, sugar content, dissolved oxygen, dissolved nitrogen, and dissolved carbon dioxide. Sensors in the exiting metabolite stream line 130 monitor and control the flow rate, concentration of metabolites, pH, temperature, sugar content, dissolved oxygen, and dissolved nitrogen. Solenoid valves S installed in the appropriate lines from other tanks and equipment insure the satisfactory and efficient operation of the bioreactor B5.

Nutrient tanks T8 and T9, in addition to supplying solenoid valves S controlled by the flow sensors in lines 138 and 130, are equipped with level controls, automatic alarms, and pH sensors. Holding tank HT15 is equipped with all the controls required to make it a self-operating but within the control of the overall process.

Controls are installed on Centrifuge C17 to make it operate automatically with holding tank HT15. The controls of other ancillary equipment such as the pH adjustment tanks, heat exchangers, hormone and vitamin tank, etc. are designed to allow them to operate automatically within the requirements of overall process.

A centrally located computer monitors, records, and controls all process variables and equipment responses required for the satisfactory operation of the process.

BIOREACTOR

The large scale bioreactor B5 is illustrated in FIGS. 3 through 7. This bioreactor B5 includes a plurality of generally vertically oriented dialysis tubes 22 arranged parallel to one another and contained within a reaction vessel 200 having removable heads 202 and 204 located at the top and bottom of the reaction vessel. The heads 202 and 204 are removably connected to a cylindrical member 206 having the cooling jackets 208 extending about the circumference.

Figure 4:
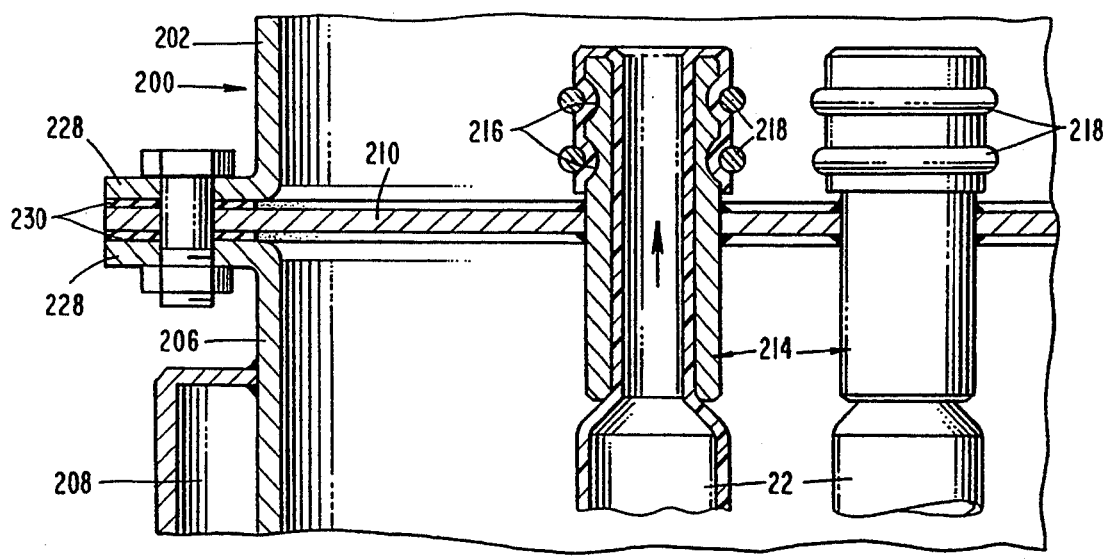
FIG. 4 is an enlarged, fragmentary, sectional view taken along line 4—4 of FIG. 3.
Figure 5:
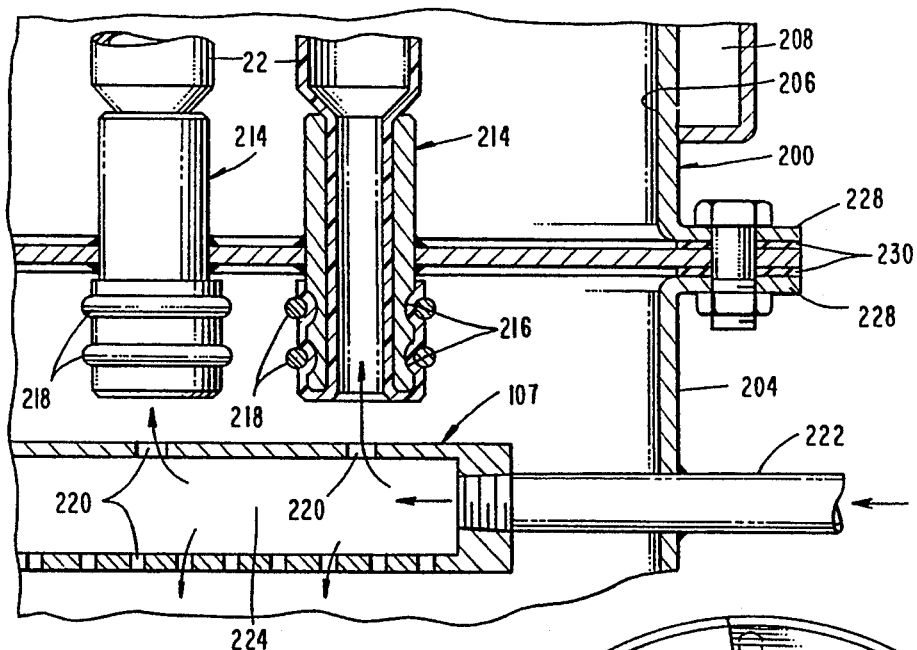
FIG. 5 is an enlarged, fragmentary, sectional view taken along line 5—5 of FIG. 3.
Figure 6:
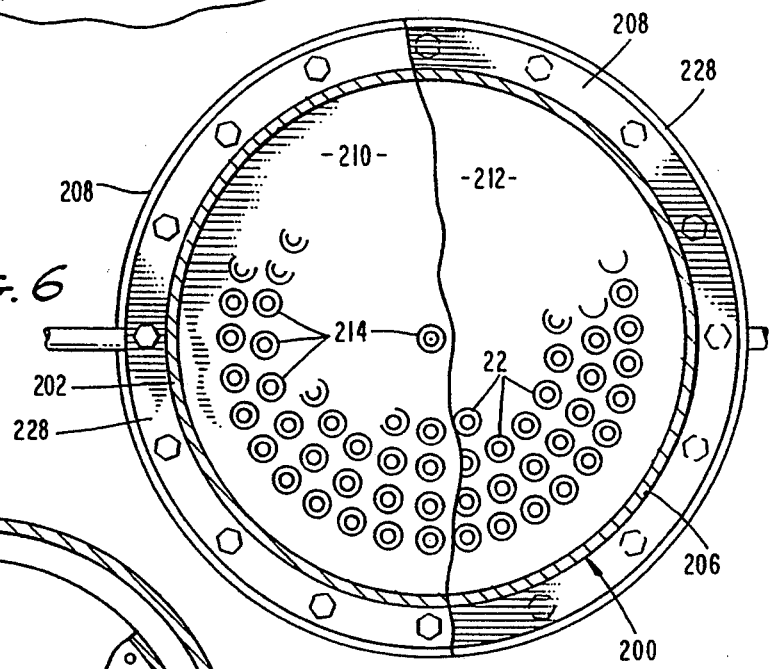
FIG. 6 is a sectional view taken along line 6—6 of FIG. 3.
Figure 7:
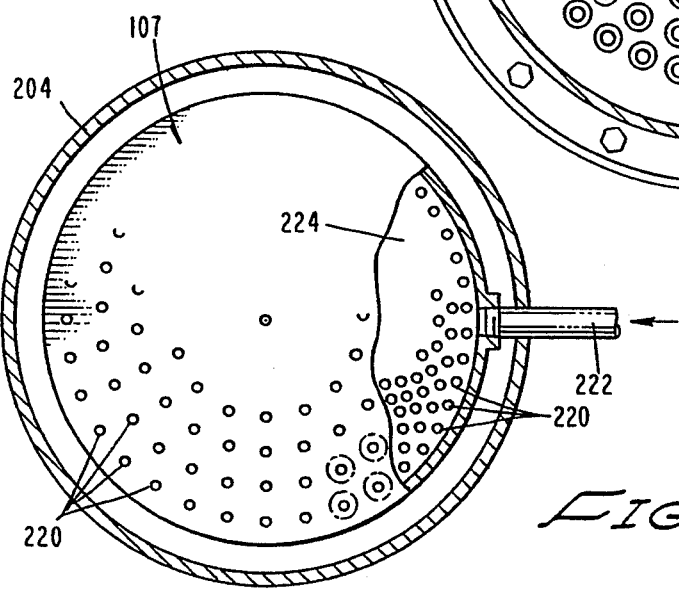
FIG. 7 is a sectional view taken along line 7—7 of FIG. 3.

The vessel 200 includes both a top and bottom plates 210 and 212. Each of these plates 210 and 212 have a plurality of nipples 214 which extend through the plates and are, for example, welded in position. The outer portion of each nipple 214 has a pair of annular groves 216 therein. As best illustrated in FIGS. 4 and 5, the tubes 22 are at their ends constricted and drawn through the nipples and folded outwardly so that end portions of the tubes cover the annular groves. Pairs of O-rings 218 are slipped over the ends of the tubes 22 and hold the tubes firmly in position.

At the bottom of the reaction vessel is the sparger 107 having a plurality of orifices 220 both in its top and bottom. Gas under pressure is forced through the gas inlet 222 to fill the interior chamber 224 of the sparger and force gas bubbles out the orifices 220. Preferably, the orifices 220 are aligned with the lower ends of the tubes so that air moves upwardly into the interior of the tubes. If an anaerobic reaction is being conducted carbon dioxide is forced through the inlet 222 rather than air. In the exterior of the vessel is an observation window 226 which allows the interior of the vessel to be observed.

In assembly, the tubes 22 are placed in position on the plates 210 and 212 and then the plates are placed between the upper and lower headers 202 and 204 with the tubes extending between the plates. The plates 210 and 212 are then bolted in position at the flange portions surrounding the headers and central cylindrical portion of the reaction vessel. Seals 230 are placed in portion between flanges 228 and the plates 210 and 212 to prevent leakage. Water flows into and from the cooling jackets 208 to regulate the temperature of the liquid on the interior of the vessel 200. The tubes 22 are immersed in the aqueous medium which is fed to the inside of the cylindrical member 206 of the vessel. The cellular material fills the head 204 and flows through the tubes 22 upwardly.

The bioreactor B5 and its controls assures: the introduction of sterile cells into the dialysis tubes, the flow of right amounts of concentrated and dilute nutrient solutions, optimum bioreactor temperature, pH, cell density, excess air or nitrogen, the removal of unused air or nitrogen and metabolic gases, the growth and removal of new cell mass, the creation and removal of metabolites, flexible dialysis tubes 22 to prevent the build-up of cells inside the walls of the dialysis tubes which prevent metabolites from crossing through the membrane.

The preferred material of construction for the body of the bioreactor B5 is 316 stainless steel. The tubes 22 are made from cellulose acetate or polysulfone of the cut-off (Daltons 500 to 500,000) required by the product grown. Any plastic material used must be autoclavable like polycarbonate or its equal.

The dimensions for bioreactor B5 to grow garlic are:
Diameter 36 inches, excluding cooling jacket.
Length: 48 inches, tube length, overall 66 inches.
Tubes: 340 ½, inch diameter
Output: 30.6 pounds (dry) per day (estimated)

The bioreactor B5 may be installed vertically. This is desirable for the following reasons: First, because the dialysis tubes 22 are flexible, and to function well, they preferably are upright. Second, because the tubes 22 are attached to the tube sheet nipples, they are installed in a special manner. Third, because air from the sparger 107 is directed through a separate nozzle into bottom of each dialysis tube where it flows upwards to be highly effective.

The bioreactor B5 is assembled in a special way with a special wire tool. The top and bottom tubes fastened to the nipples in the position they will occupy in the assembled bioreactor. Then, plates 210 and 212 and cylinder member 206 are placed on a raised jig to make tubing easy. The dialysis tubes 22 are precut to 54" and installed one at a time by a wire tool which is inserted inside and clipped to the top and bottom of the tube. Tube and tool are thrust through the top tube nipple 214, down through the matching bottom tube nipple. The clip from the top of the tube is removed and the tube folded back over the nipple and fastened in the Grooves 216 with the "O" rings 218. Then, the bottom part of the tube 22 is fastened in the same way after a little slack has been left to allow the tube to flex and move slightly. Care is taken not to leave too much slack otherwise the tubes 22 will rub against each other and wear out prematurely.

When all the tubes have been installed, the top and bottom headers 202 and 204 are gasketed with seals 230 and bolted in place, and the bioreactor B5 is ready to be used.

j) The bioreactor B5 is designed to be taken apart easily so that its tubes 22 can be changed with minimum effort.

k) The working or exposed length of the dialysis tube 22 are 202 and 204 slightly Greater than the actual distance between the headers to allow the bioreactor B5 to be assembled. However, care must be taken not to make the tubes 22 so long that they rub against each other.

l) Four glass windows 226 eight inches in diameter allow a view of what is occurring inside the bioreactor.

SCOPE OF THE INVENTION

The above description discloses the best mode contemplated for carrying out this invention. The invention is, however, susceptible to modifications, for example, in the preparation of plant cells, the chemicals used, in the sizes of the equipment used, and alternate process steps from those described in the examples and illustrated in the drawing. Consequently, it is not the intention to limit this invention to the particular embodiments disclosed. On the contrary, the intention is to cover all modifications and alternates coming within the spirit and scope of the invention as generally expressed by the following claims.

I claim:

1. An in vitro process for growing living cellular material comprising of the steps of:
    a) filling a flexible, semi-permeable, tubular membrane with live cells in a concentration range of from $10^2$ to $10^7$ cells per milliliter, said tubular membrane having an exclusion range of from 500 to 1,000,000 Daltons, a length of from 1 to 8 feet, and a diameter of from 0.025 to 3.0 inches, said tubular membrane having a wall to which cellular material tends to adhere, said wall being periodically agitated to remove cell material adhering to it,
    b) immersing the tubular membrane in an aqueous medium,
    c) continuously feeding a concentrated aqueous nutrient solution to the live cells inside the tubular membrane,
    d) controlling conditions within the tubular membrane to promote rapid growth of the live cells by maintaining
        (i) the temperature of the cells and aqueous medium in the range of from 50 to 75 degrees Fahrenheit,
        (ii) the pH of the concentrated nutrient solution and aqueous medium essentially equal to each other and in the range of from 3.0 to 11.0,
        (iii) the velocity of the concentrated nutrient solution through the tubular membrane in the range of from 0.005 to 3.0 feet per minute, and
        (iv) the velocity of the aqueous medium over the exterior of the tubular membrane in the range of from 0.005 to 5.0 feet per minute, and
    d) withdrawing the cells from the tubular membrane at a controlled rate to maintain the number of individual cells within the membrane in the range of from $10^2$ to $10^{10}$ cells per milliliter, and
    wherein immature cells are removed and retained in a holding tank to grow to mature size, and wherein the cells are separated from concentrated nutrient solution associated therewith, and the nutrient solution is recycled to the holding tank.

2. The process of claim 1 including the step of recycling a portion of the withdrawn cells to the tubular membrane.

3. The process of claim 1 wherein the nutrient solution includes growth promoters which are filtered to remove contaminants.

4. The process of claim 1 wherein the pH is continuously monitored and adjusted to maintain said pH in said range.

5. The process of claim 1 wherein the aqueous medium is continuously removed from the vicinity of the membrane and replenished.

6. The process of claim 5 wherein the aqueous medium used to replenish is fresh aqueous medium or recycled aqueous medium.

* * * * *